United States Patent [19]

Smits

[11] 4,311,153
[45] Jan. 19, 1982

[54] SCREW-IN LEAD HAVING LEAD TIP WITH MEMBRANE

[75] Inventor: Karel F. A. A. Smits, Oirsbeek, Netherlands

[73] Assignee: Medtronic, Inc., Minneapolis, Minn.

[21] Appl. No.: 192,265

[22] Filed: Sep. 30, 1980

[51] Int. Cl.³ ............................................. A61N 1/04
[52] U.S. Cl. ................................. 128/785; 128/419 P
[58] Field of Search ..................... 128/784, 785, 419 P

[56] References Cited

U.S. PATENT DOCUMENTS

| 4,046,151 | 9/1977 | Rose | 128/419 P |
|---|---|---|---|
| 4,106,512 | 8/1978 | Bisping | 128/419 P |
| 4,142,531 | 3/1979 | Magovern et al. | 128/419 P |
| 4,146,036 | 3/1979 | Dutcher et al. | 128/419 P |
| 4,217,913 | 8/1980 | Dutcher | 128/419 P |

Primary Examiner—William E. Kamm
Attorney, Agent, or Firm—John L. Rooney; Joseph F. Breimayer

[57] ABSTRACT

A screw-in endocardial transvenous pacing lead having a lead tip with a sealing membrane. The lead is chronically affixed by a helical fixation coil having a pointed tip which is rotatably advanced through a helical lumen in the lead tip into the endocardial tissue. During transvenous insertion, the helical fixation coil is retracted into a chamber to protect against damage of the vein. A sealing membrane is positioned perpendicularly within the helical lumen of the lead tip preventing ingress of body fluids. The sealing membrane is of silicon rubber with a polyurethane coating on either side. Upon being properly located within the heart, the helical fixation coil is rotatably extended. The pointed tip of the helical fixation coil punctures the sealing membrane normal to its direction of travel. The sealing membrane provides a seal around the helical fixation coil.

8 Claims, 10 Drawing Figures

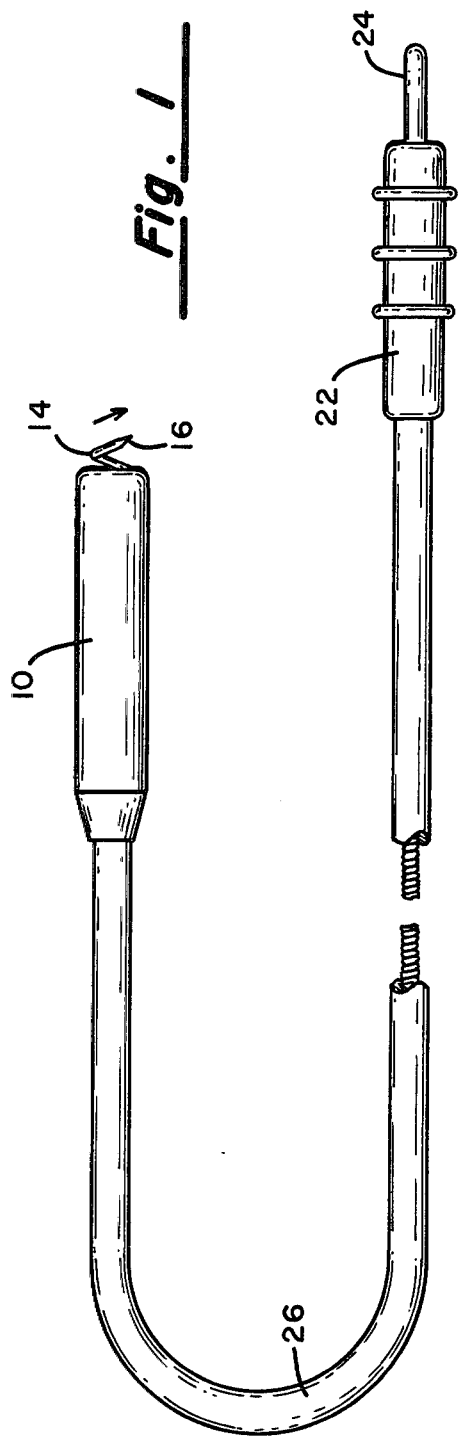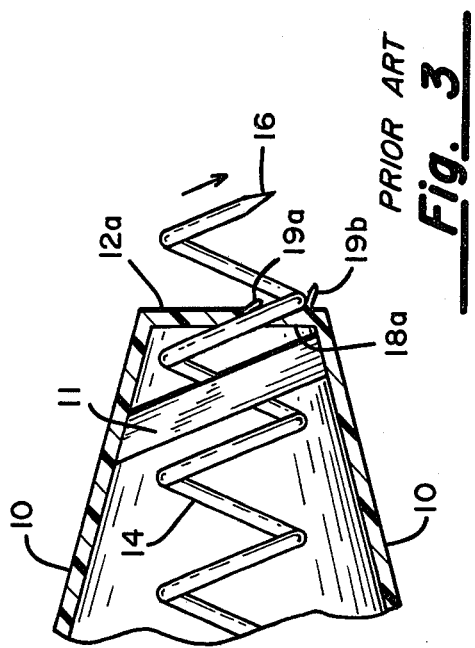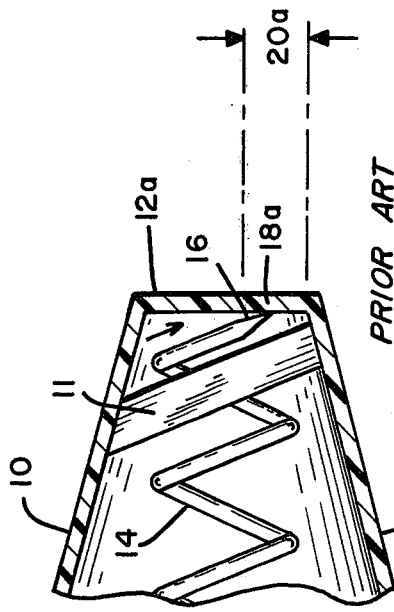

SCREW-IN LEAD HAVING LEAD TIP WITH MEMBRANE

BACKGROUND OF THE INVENTION

1. Field of the Invention

The present invention relates generally to medical electronic devices and more specifically relates to cardiac pacing leads.

2. Discussion of the Prior Art

A major advance in the development of endocardial pacing leads is taught by Bisping in U.S. Pat. No. 4,106,512. The Bisping invention provides a helical fixation device to be screwed into the endocardial tissue thereby securing the distal end of the lead both acutely and chronically. A major problem with the endocardial screw-in lead of Bisping and his successors has been obtaining a proper seal at the distal end of the lead to prevent ingress of body fluid into the lead body. At column 5, lines 23–27, Bisping describes the use of a medical adhesive to effect the desired seal.

Copending U.S. patent application Ser. No. 69,948, now abandoned, of Dutcher, et al, assigned to the assignee of the present invention describes a guide seal using a sealing membrane of silicon rubber. Common to the sealing techniques taught by Bisping, Dutcher, et al, and others studied is the problem of leakage during chronic implantation.

SUMMARY OF THE INVENTION

The present invention involves an improved seal to greatly curtail this leakage problem. The solution is obtained via use of a sealing membrane of silicon rubber with a covering of polyurethane. This "sandwich" configuration has been found to be more effective as the sealing membrane tends to retain its resiliency over greater angular displacement at the puncture. A second aspect is locating the sealing membrane within the helical lumen to cause the helical fixation coil to puncture the sealing membrane at an angle normal to its direction of travel. This provides a more uniform puncture.

BRIEF DESCRIPTION OF THE DRAWINGS

FIG. 1 is a plan view of the screw-in lead with the helical fixation coil extended.

FIG. 2 is a schematic view of a prior art screw-in lead tip with helical fixation coil retracted.

FIG. 3 is a schematic view of a prior art screw-in lead tip with helical fixation coil extended.

DETAILED DESCRIPTION OF THE PREFERRED EMBODIMENT

Figure 4:
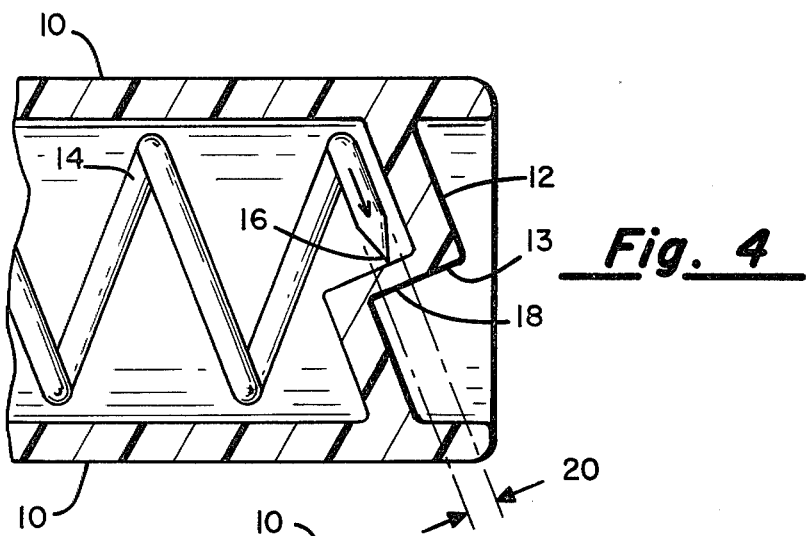
FIG. 4 is a schematic view of a screw-in lead tip employing the present invention with helical fixation coil retracted.

The present invention is seen as being incorporated into a screw-in lead as taught by Bisping in U.S. Pat. No. 4,106,512, which is hereby incorporated by reference. However, it is anticipated that the present invention will also be used with a screw-in lead similar to that taught by Dutcher, et al, in U.S. Pat. No. 4,146,036 which is also incorporated by reference. Those of ordinary skill in the art will be readily able to apply the present invention to screw-in leads of other types as well.

FIG. 1 is a plan view of a screw-in lead employing the present invention. Lead body 26 is of an insulator substantially inert to body fluids. A conductor within lead body 26 couples connector pin 24 at the proximal end to helical fixation coil 14 at the distal end. Lead tip 10 is inserted into the heart via well known transvenous insertion techniques with helical fixation coil 14 totally retracted within lead tip 10 such that pointed tip 16 is not exposed to render possible harm to tissues while in transit. Helical fixation coil 14 may be rotatably extended or retracted by rotation of connector pin 24. Connector body 22 serves to seal the proximal end from ingress of body fluids upon insertion into a pulse generator (not shown).

FIG. 2 is a highly enlarged schematic view of the distal tip of a prior art screw-in lead. Helical fixation coil 14 is shown in the retracted position. Sealing membrane 12a prevents ingress of body fluids. It can be seen that upon extending helical fixation coil 14, sealing membrane 12a is punctured at point 18a producing a puncture whose projection on sealing membrane 12a is shown as dimension 20a. That means that sealing membrane 12a is disturbed along dimension 20a. Member 11 is a guiding wire for extension of the fixation coil upon rotation of the fixation coil.

FIG. 3 shows the same prior art structure after extending helical fixation coil 14. The puncture at point 18a is in the direction of travel of pointed tip 16. Because sealing membrane 12a is normal to the main axis of lead tip 10, the puncture at point 18a is at an acute angle to the surface of seal 12a. This tends to cause puncture flaps 19a and 19b to be of unequal size since the penetration of pointed tip 16 exerts unequal forces about point 18a as sealing membrane 12a is punctured.

FIG. 4 is a schematic diagram of a similar lead tip employing the present invention. Helical sealing membrane 12 has a formed portion 13 which is located normal to the direction of travel of pointed tip 16. As pointed tip 16 punctures formed portion 13 of sealing membrane 12, the puncture has a projection on formed portion 13 equal to dimension 20. A comparison of FIGS. 2 and 4 shows that dimension 20a (See FIG. 2) is significantly larger than dimension 20 (See FIG. 4) because of the difference in puncture angle. The practical significance is that dimension 20a must be sealed in FIG. 2 whereas only dimension 20 need be sealed in FIG. 4. The thickness of the helical membrane 12, except formed portion 13, is enlarged to the size of the spacing between the helical coil electrode, in order to serve as a helical guide for the helical coil electrode when being extended or retracted upon rotation.

Figure 5:
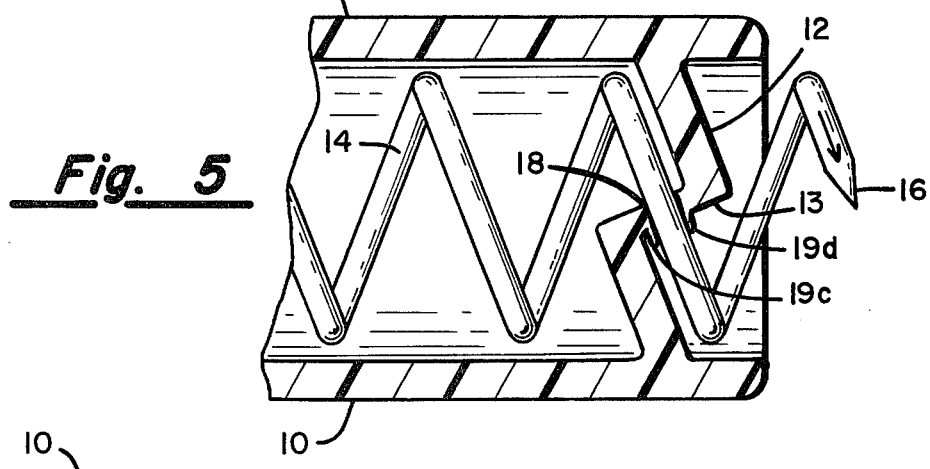
FIG. 5 is a schematic view of a screw-in lead tip employing the present invention with helical fixation coil extended.

FIG. 5 shows the structure with helical fixation coil extended. Because pointed tip 16 punctures formed portion 13 at a right angle, equal force is exerted in all directions. This tends to cause flaps 19c and 19d to be of equal size. Perhaps even more importantly, flaps 19c and 19d are each nearly perpendicular to formed portion 13 causing maximum chronic sealing. A comparison with FIG. 3 shows that flap 19a is at an acute angle and flap 19b is at an obtuse angle. This disparity greatly affects chronic sealing and impacts resiliency preventing effective sealing. This configuration can be chosen, if the complete tip or the membrane 12 and formed portion 13 are made of silicon rubber.

Figure 6:
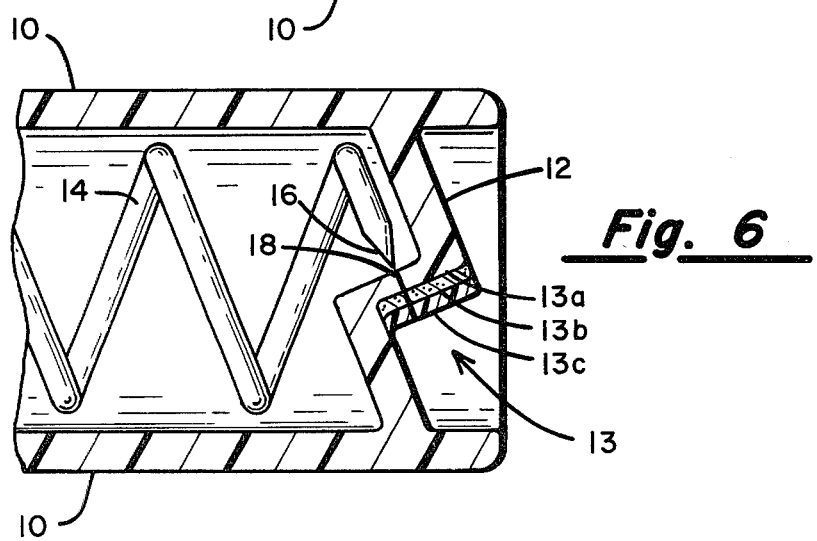
FIG. 6 is a schematic view of a sealing membrane.

FIG. 6 is a schematic drawing showing that the formed portion 13 of sealing membrane 12 actually contains three layers. Layers 13a and 13c are polyurethane or other thermoplastic material. Layer 13b is a non-stress relaxing material such as silicon rubber or medical adhesive. This combination has been shown to provide good chronic sealing, if the membrane 12 and housing 10 are made of polyurethane or other thermoplastic material.

Figure 7:
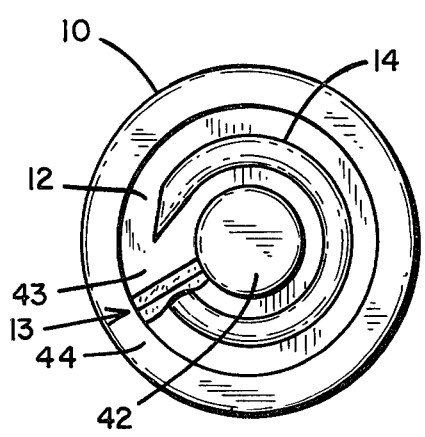
FIG. 7 is a front view of a screw-in lead tip.

FIG. 7 is a front view of the distal tip of lead tip 10. Lead tip 10 is molded of polyurethane or other suitable material. From the distal end, lead tip 10 has a cylindrical lumen 43 surrounded by pillar 42 and outer housing 44, and bottomed by the sealing membranes 12 and 13. Upon being extended, helical fixation coil 14 punctures sealing formed portion 13 of helical membrane 12 and proceeds into cylindrical lumen 43 and outward into the endocardium. Pillar 42, cylindrical lumen 43, and outer housing 44 are the distal end of a cylindrical lumen inside of lead tip 10 through which helical fixation coil 14 travels.

Figure 8:
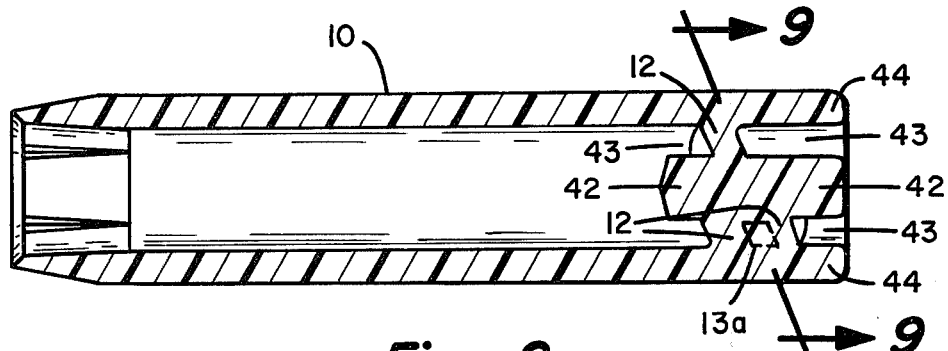
FIG. 8 is a side sectional view of the screw-in lead tip.

FIG. 8 is a side sectional view of lead tip 10, which is molded of polyurethane as explained above. The cylindrical lumen is seen as comprised of points 43, and pillar 42. This cylindrical lumen and helical membrane 12 guide the movement of helical fixation coil 14 (not shown in this view). Formed portion 13a of sealing membrane 12 is shown by the dotted lines between the extremes of sealing membrane 12 in axial direction, and between pillar 12 and housing 44 in radial direction. Formed portion 13a is originally molded into the lead tip. Through formed portion 13a in a direction approximately perpendicular to the sectional plane, the helical coil electrodes will be punctured.

Figure 9:
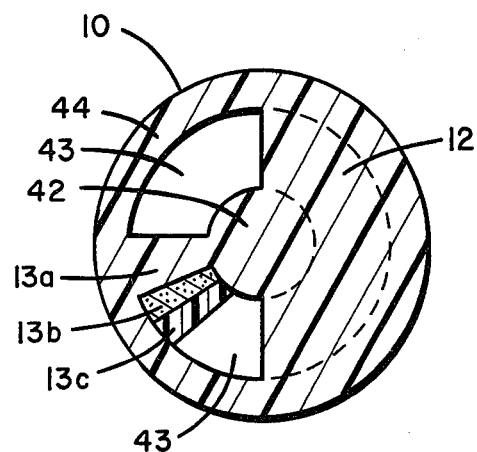
FIG. 9 is a front sectional view of the screw-in lead tip.

FIG. 9 is a sectional view taken perpendicular to the main axis of lead tip 10 and parallel to formed portion 13a. Because formed portion 13 is at an acute angle relative to the plane of the sectional view, the layers 13a, 13b and 13c are all clearly visible. Notice that layer 13a is as originally molded into lead tip 10 being of the same material. Layer 13b is deposited onto layer 13a. Layer 13b is preferably silicon rubber or medical adhesive. Layer 13c is subsequently deposited on layer 13b. Layer 13c is preferably polyurethane or other thermoplastic material.

Figure 10:
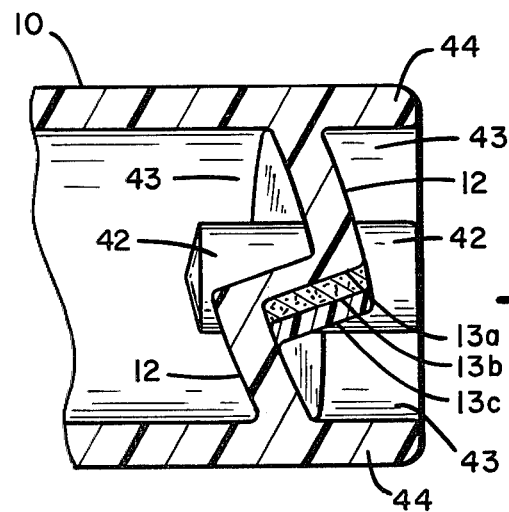
FIG. 10 is a partial cutaway view of the sealing membrane.

FIG. 10 shows a sectional cutaway view of sealing membrane 12 viewed parallel to the plane of formed portion 13. Cylindrical lumen 43 is shown. Layer 13a is shown as a molded portion of lead tip 10. Layer 13b is deposited on layer 13a distal to layer 13a. Layer 13c is subsequently deposited on layer 13b.

What is claimed is:
1. An implantable lead comprising:
   a conductor having a proximal end and a distal end;
   an insulator having a proximal end and a distal end;
   a chamber attached to said distal end of said insulator having an aperture;
   a fixation device rotatably attached to said chamber whereby rotation of said fixation device is a first direction causes said fixation device to move proximal relative to said aperture and rotation of said fixation device in a second direction causes said fixation device to move distal relative to said aperture; and
   a seal attached to said chamber at said aperture having a shape causing a portion of said fixation device to frictionally engage said seal in a direction substantially normal to the direction of motion of said portion of said fixation device when said fixation device is rotated in said first and second direction.
2. An implantable lead according to claim 1 wherein said fixation device is a helix.
3. An implantable lead according to claim 1 wherein said seal further comprises:
   a non-stress relaxing material having a first side and a second side; and
   a covering of thermoplastic material attached to said first side and said second side of said non-stress relaxing material.
4. An implantable lead according to claim 3 wherein said non-stress relaxing material is silicon rubber.
5. An implantable lead according to claim 4 wherein said covering of thermoplastic material is polyurethane.
6. An implantable lead according to claim 1, 2, 3, 4 or 5 wherein said conductor is attached to said fixation device whereby rotation of said conductor is said first direction causes said fixation device to rotate in said first direction and rotation of said conductor in said second direction causes said fixation device to rotate in said second direction.
7. An implantable lead according to claim 1, 2, 3, 4 or 5 further comprising:
   a stylet loosely inserted within said conductor; and
   means attached to said stylet and said fixation device for coupling torque applied to said stylet to said fixation device.
8. In a screw-in endocardial pacing lead with a distal end having a helically shaped fixation device with at least one coil and a sharp point and having a chamber with an aperture located at said distal end of said pacing lead into which and from which said helical coil may be rotationally projected, the improvement comprising:
   a guide seal attached to said chamber at said aperture at an angle perpendicular to the direction of movement of said sharp point of said helically shaped fixation device.

* * * * *

UNITED STATES PATENT AND TRADEMARK OFFICE
CERTIFICATE OF CORRECTION

PATENT NO. : 4,311,153
DATED : January 19, 1982
INVENTOR(S) : Karel F. A. A. Smits It is certified that error appears in the above-identified patent and that said Letters Patent are hereby corrected as shown below:

Claim 1, line 8, "is" should be --in--.

Claim 6, line 35, "is" should be --in--.

Signed and Sealed this

Fourteenth Day of December 1982

[SEAL]

Attest:

Attesting Officer

GERALD J. MOSSINGHOFF

Commissioner of Patents and Trademarks